(12) United States Patent
Furuta et al.

(10) Patent No.: US 10,001,432 B2
(45) Date of Patent: Jun. 19, 2018

(54) HARDNESS TEST APPARATUS AND HARDNESS TESTING METHOD

(71) Applicant: MITUTOYO CORPORATION, Kanagawa (JP)

(72) Inventors: Eiji Furuta, Sagamihara (JP); Makoto Kaieda, Miyazaki (JP); Akira Takada, Yokohama (JP)

(73) Assignee: MITUTOYO CORPORATION, Kanagawa (JP)

( * ) Notice: Subject to any disclaimer, the term of this patent is extended or adjusted under 35 U.S.C. 154(b) by 0 days. days.

(21) Appl. No.: 15/255,753

(22) Filed: Sep. 2, 2016

(65) Prior Publication Data

US 2017/0074764 A1 Mar. 16, 2017

(30) Foreign Application Priority Data

Sep. 10, 2015 (JP) .................. 2015-178034

(51) Int. Cl.
*G06K 9/00* (2006.01)
*G01N 3/42* (2006.01)

(52) U.S. Cl.
CPC ....... *G01N 3/42* (2013.01); *G01N 2203/0098* (2013.01); *G01N 2203/0647* (2013.01);
(Continued)

(58) Field of Classification Search
None
See application file for complete search history.

(56) References Cited

U.S. PATENT DOCUMENTS

| 8,566,735 B2 | 10/2013 | Takemura et al. |
| 8,849,588 B2 | 9/2014 | Sawa et al. |

(Continued)

FOREIGN PATENT DOCUMENTS

| JP | 2003-166923 A | 6/2003 |
| JP | 2012-78306 A | 4/2012 |
| JP | 2014126417 | * 7/2014 |

OTHER PUBLICATIONS

U.S. Appl. No. 15/255,782 to Fumihilco Koshimizu et al., filed Sep. 2, 2016.

(Continued)

*Primary Examiner* — Sumati Lefkowitz
*Assistant Examiner* — David Perlman
(74) *Attorney, Agent, or Firm* — Greenblum & Bernstein, P.L.C.

(57) ABSTRACT

The present invention includes: an image capturer capturing an image of the sample to be measured; an image acquirer acquiring image data of the sample captured by the image capturer; a pattern searcher performing, on the image data of the sample acquired by the image acquirer, pattern searching process using a pattern image selected based on the sample and identifying a position in the image matching the pattern image; a profile extractor extracting a profile of the sample based on the position in the image identified by the pattern searcher; a calculator calculating a hardness measurement position of the sample based on the profile extracted by the profile extractor; and a measurer executing hardness testing on the sample based on the hardness measurement position calculated by the calculator and measuring the hardness of the sample.

3 Claims, 10 Drawing Sheets

(52) U.S. Cl.
CPC ............... *G01N 2203/0682* (2013.01); *G06T 2207/10004* (2013.01); *G06T 2207/30108* (2013.01)

(56) References Cited

U.S. PATENT DOCUMENTS

2014/0177937 A1* 6/2014 Ariga ............... G01N 3/068
 382/141
2015/0287177 A1 10/2015 Kaieda et al.
2016/0093068 A1 3/2016 Sugai et al.

OTHER PUBLICATIONS

U.S. Appl. No. 15/251,324 to Takeshi Sawa et al., filed Aug. 30, 2016.
U.S. Appl. No. 15/251,295 to Takeshi Sawa et al., filed Aug. 30, 2016.

* cited by examiner

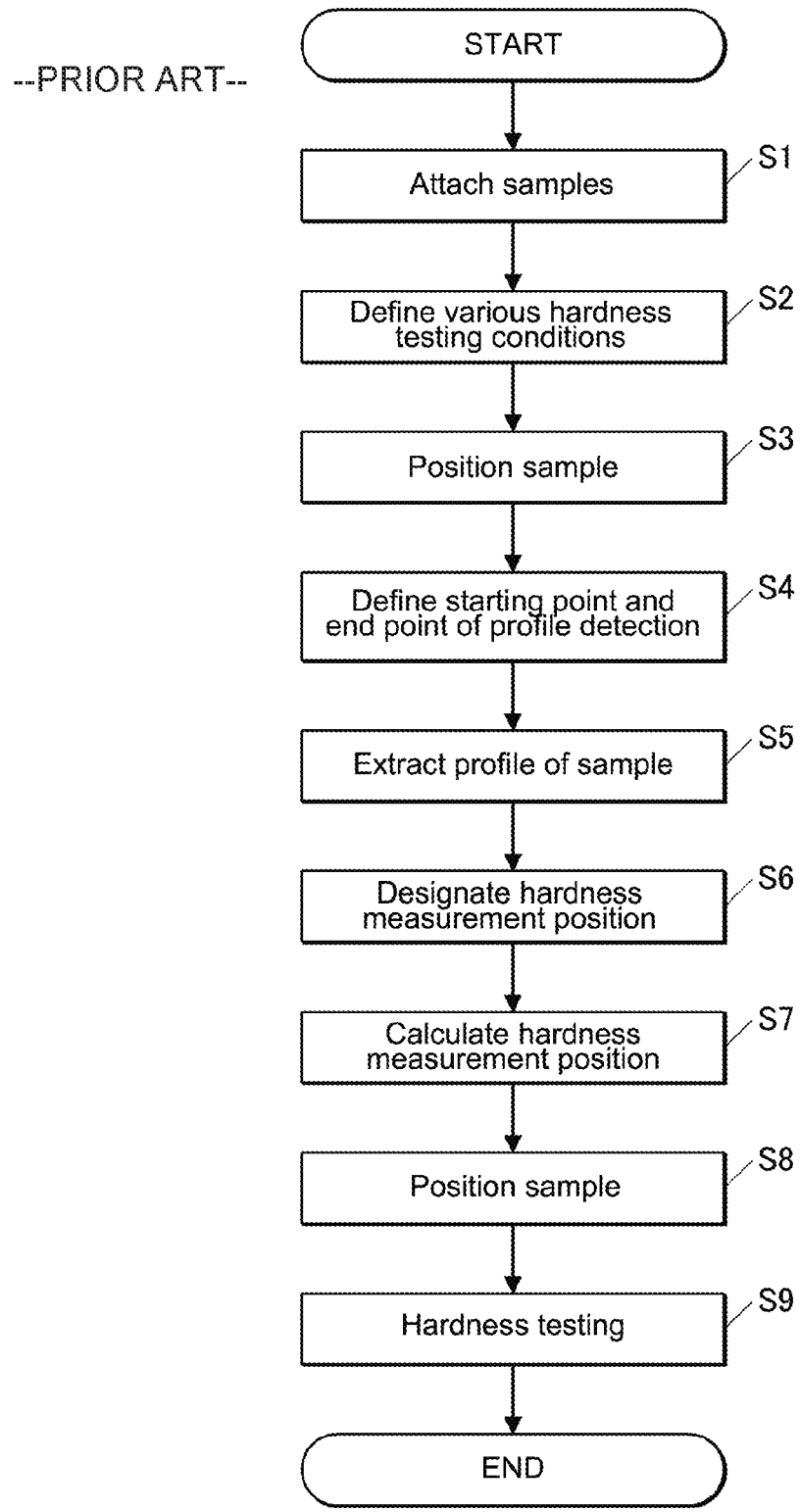
Fig. 12 --PRIOR ART--

HARDNESS TEST APPARATUS AND HARDNESS TESTING METHOD

CROSS-REFERENCE TO RELATED APPLICATIONS

The present application claims priority under 35 U.S.C. § 119 of Japanese Application No. 2015-178034, filed on Sep. 10, 2015, the disclosure of which is expressly incorporated by reference herein in its entirety.

BACKGROUND OF THE INVENTION

1. Field of the Invention

The present invention relates to a hardness tester and to a hardness testing method.

2. Description of Related Art

A conventional hardness tester is known which measures hardness of a sample based on dimensions of an indentation formed by pressing an indenter against the sample (work piece) with a predetermined test force. For example, a Vickers hardness tester measures a length of diagonal lines of an indentation formed by pressing a quadrangular pyramidal indenter into a surface of the sample, and calculates hardness based on the measured length of the diagonal lines of the indentation (see, for example. Japanese Patent Laid-open Publication No. 2003-166923).

Hardness testing is conducted in a conventional hardness tester as shown by a flow chart in FIG. 12. Specifically, an operator first sets a sample on a tester main body (step S1). Next, the operator defines various conditions of the hardness test (for example, material of the sample, test force, or magnification power of a field lens) (step S2). The operator then displaces the sample and positions it so as to allow a hardness testing site to be displayed on a monitor (step S3). Next, the operator designates a starting point and end point of profile detection of the sample on the monitor (step S4). Next, the process switches to a CPU of a controller as agent, and the CPU continuously executes profile detection from the starting point to the end point of the profile detection of the sample and extracts the profile of the sample (step S5). The process then switches once again to the operator as agent, and the operator designates both a coordinate system having the extracted profile as a reference, and also hardness measurement positions (a measurement pattern) of the sample (step S6). The operator also inputs parameters such as a measurement interval. Next, the process switches once again to the CPU as agent, and the CPU calculates the hardness measurement positions of the sample based on the extracted profile and the designated hardness measurement positions of the sample (step S7). The CPU then displaces the sample to position it such that the calculated hardness measurement position is directly below the field lens (step S8). Next, the CPU performs the hardness test (step S9). Specifically, the CPU creates an indentation at the hardness measurement position, automatically reads the indentation formed by the indentation creation, and measures the hardness of the sample.

However, in the procedural flow of the conventional hardness testing described above, before performing the process to designate the starting point and end point of the profile detection of the sample on the monitor, a process is performed in which the sample is positioned so as to allow the hardness testing site to be displayed on the monitor. However, because the operator performs this process by manipulating a joystick, for example, while observing the sample, the process provides inferior usability and poor work efficiency. Also, in the procedural flow of the conventional hardness testing described above, processes having the operator as agent are interspersed with processes having the CPU as agent, which also contributes to inferior usability and poor work efficiency.

SUMMARY OF THE INVENTION

The present invention provides a hardness tester and a hardness testing method having favorable usability and capable of improving work efficiency.

One aspect of the present invention to address the above is a hardness tester measuring hardness of a sample by loading a predetermined test force on the sample with an indenter to form an indentation in a surface of the sample, then measuring dimensions of the indentation. The hardness tester includes: an image capturer capturing an image of the sample to be measured; an image acquirer acquiring image data of the sample captured by the image capturer; a pattern searcher performing, on the image data of the sample acquired by the image acquirer, a pattern searching process using a pattern image selected based on the sample and identifying a position in the image matching the pattern image; a profile extractor extracting a profile of the sample based on the position in the image identified by the pattern searcher; a calculator calculating a hardness measurement position of the sample based on the profile extracted by the profile extractor; and a measurer executing hardness testing on the sample based on the hardness measurement position calculated by the calculator and measuring the hardness of the sample.

In another aspect of the present invention, the hardness tester includes a memory storing test information defining a starting point and end point of profile detection of the sample, as well as the hardness measurement position of the sample, with reference to the pattern image. The profile extractor extracts the profile of the sample based on the position in the image specified by the pattern searcher, and on the test information stored in the memory. The calculator calculates the hardness measurement position of the sample based on the profile extracted by the profile extractor, and on the test information stored in the memory.

Another aspect of the present invention is a hardness testing method of a hardness tester measuring hardness of a sample by loading a predetermined test force on the sample with an indenter to form an indentation in a surface of the sample, then measuring dimensions of the indentation. The hardness testing method includes: image acquisition acquiring image data of the sample captured by an image capturer capturing an image of the sample to be measured; pattern searching performing, on the image data of the sample acquired in the image acquisition, a pattern searching process using a pattern image selected based on the sample and identifying a position in the image matching the pattern image; profile extraction extracting a profile of the sample based on the position in the image identified in the pattern searching; calculation calculating a hardness measurement position of the sample based on the profile extracted in the profile extraction; and executing hardness testing on the sample based on the hardness measurement position calculated in the calculation and measuring the hardness of the sample.

According to the present invention, usability and work efficiency can be improved.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 12 is a flow chart illustrating a hardness testing process performed by a conventional hardness tester.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the forms of the present invention may be embodied in practice.

Figure 1:
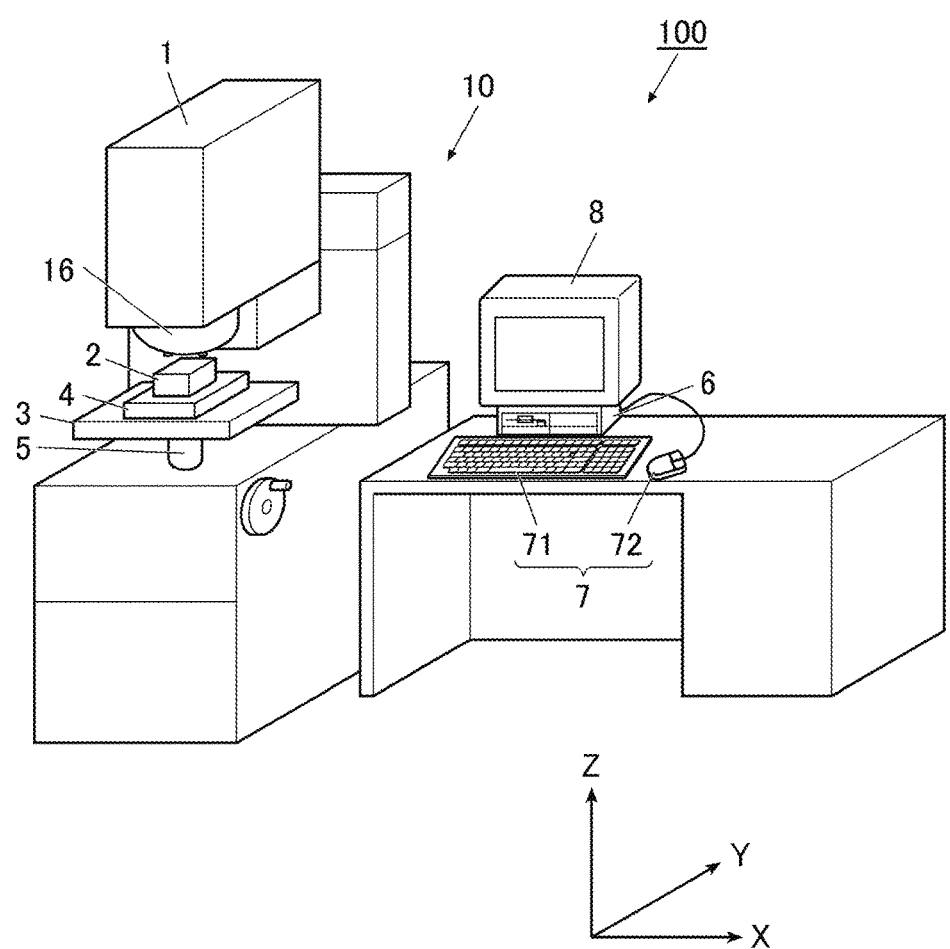
FIG. 1 is a perspective view illustrating an overall configuration of a hardness tester according to the present invention.

An embodiment of the present invention is described in detail below with reference to the drawings. Moreover, in the following description, an X direction is a left-right direction, a Y direction is a front-back direction, and a Z direction is an up-down direction in FIG. 1. In addition, an X-Y plane is a horizontal plane.

A hardness tester 100 is a Vickers hardness tester, for example, that includes an indenter 14a (see FIG. 3) having a square planar shape. As shown in FIGS. 1 to 4, the hardness tester 100 is configured to include a tester main body 10, a controller 6, a console 7, and a monitor 8.

Figure 2:
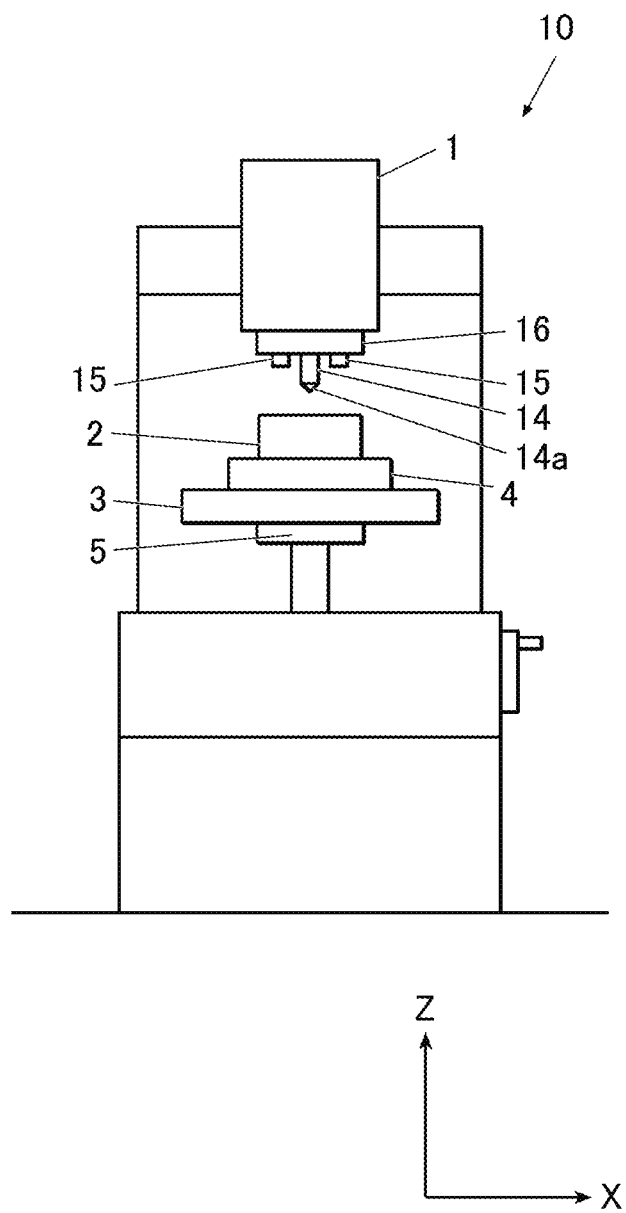
FIG. 2 is a schematic view illustrating a tester main body of the hardness tester according to the present invention.

As shown in FIG. 2, the tester main body 10 includes a hardness measurer 1 measuring hardness of a sample S; a sample stage 2 on which the sample S is mounted and fixed in place, the sample S being resin-molded around a sample to be measured (hereafter referred to as a test sample); an XY stage 3 displacing the sample stage 2; an AF stage 4 enabling focusing on a surface of the sample S; and an elevator mechanism 5 raising and lowering the sample stage 2 (the XY stage 3 and the AF stage 4).

Figure 3:
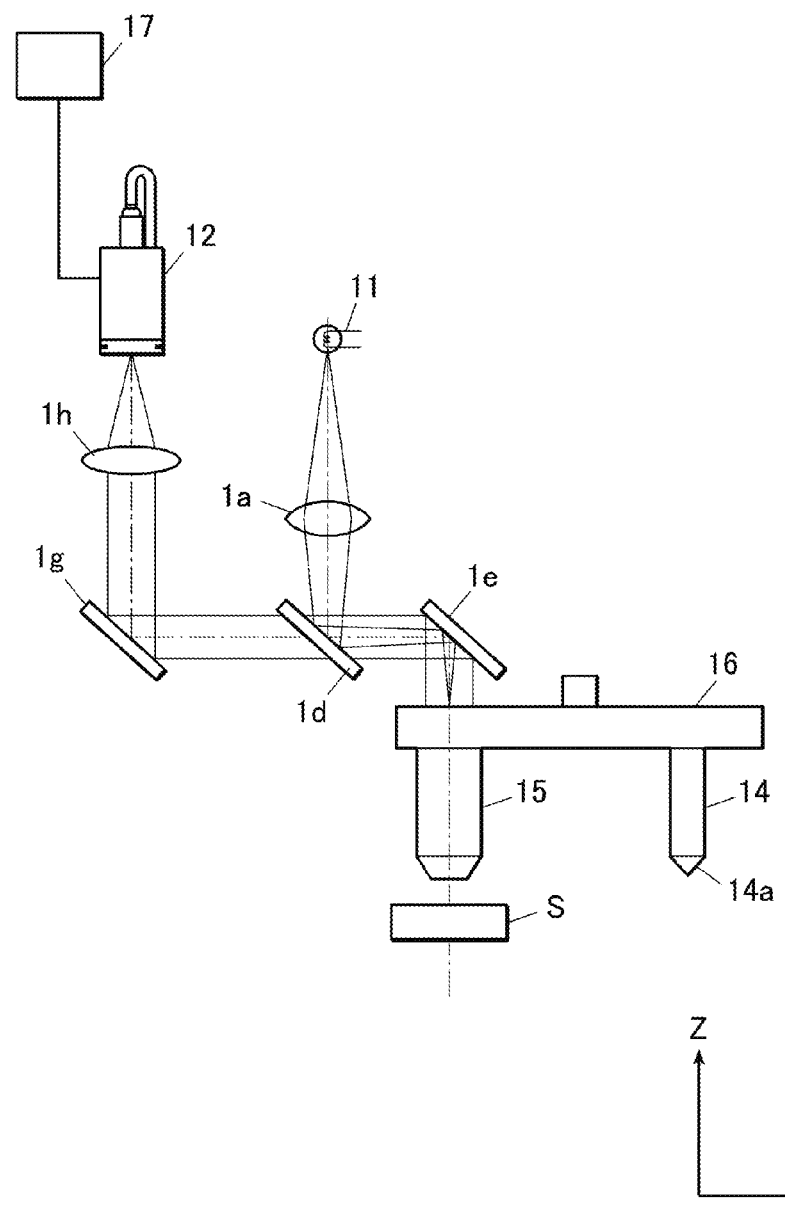
FIG. 3 is a schematic view illustrating a hardness measurer of the hardness tester according to the present invention.

As shown in FIG. 3, the hardness measurer 1 is configured with an illuminating device 11 illuminating the surface of the sample S; a CCD camera 12 capturing an image of the surface of the sample S; and a turret 16. The turret 16 includes an indenter column 14, which includes the indenter 14a, and a field lens 15. The turret 16 is capable of switching between the indenter column 14 and the field lens 15 by rotating.

The illuminating device 11 shines a light to illuminate the surface of the sample S. The light shone by the illuminating device 11 reaches the surface of the sample S via a lens 1a, a half mirror 1d, a mirror 1e, and the field lens 15.

Based on reflected light input from the surface of the sample S via the field lens 15, the mirror 1e, the half mirror 1d, a mirror 1g, and a lens 1h, the CCD camera 12 obtains image data by capturing an image of the surface of the sample S as well as an indentation formed in the surface of the sample S by the indenter 14a. The CCD camera 12 then outputs the acquired image data to the controller 6 via a frame grabber 17, which is capable of simultaneously accumulating and storing a plurality of frames of image data. Thus, the CCD camera 12 is an image capturer in the present invention.

The indenter column 14 is displaced toward the sample S placed on the sample stage 2 by a load mechanism (not shown in the drawings), which is driven in response to a control signal output by the controller 6. The indenter 14a, provided on a forefront end of the indenter column 14, is pressed against the surface of the sample S with a predetermined test force. The present embodiment uses a quadrangular pyramidal Vickers indenter (with opposing angles of 136±0.5°) as the indenter 14a.

The field lens 15 is a collective lens, each lens being configured with a different magnification. A plurality of the field lenses 15 are retained on a bottom surface of the turret 16. The field lens 15 is situated above the sample S by rotating the turret 16. Thereby, the light shone by the illuminating device 11 uniformly illuminates the surface of the sample S.

The turret 16 is configured to enable the indenter column 14 and the plurality of field lenses 15 to be attached to the bottom surface thereof. The turret 16 is also configured to be capable of positioning any one of the indenter column 14 and the plurality of field lenses 15 above the sample S by rotating the turret 16 centered around a Z-axis direction. Specifically, the indentation can be formed in the surface of the sample S by positioning the indenter column 14 above the sample S, and the formed indentation can be observed by positioning the field lenses 15 above the sample S.

Figure 5:
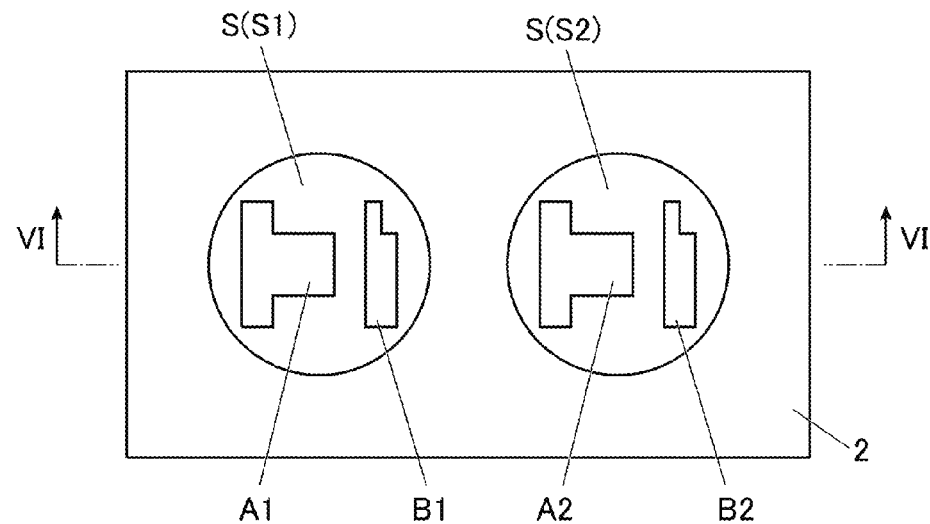
FIG. 5 is a plan view illustrating an exemplary state in which a sample is mounted on a sample stage.
Figure 6:
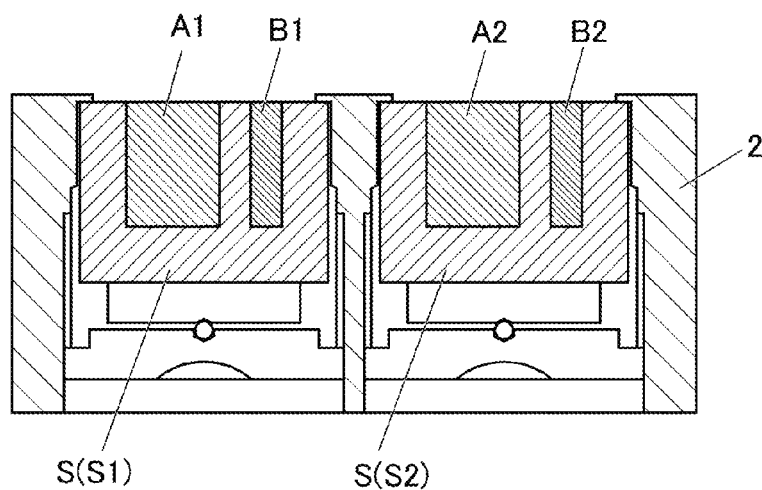
FIG. 6 is a cross-sectional exemplary view along a line VI-VI in FIG. 5.

The sample S, which is resin molded around the test sample, is mounted and fixed in place on the sample stage 2. In the present embodiment, as shown in FIGS. 5 and 6, two samples S (S1 and S2) are embedded in the sample stage 2 such that the surface of the sample stage 2 and the surfaces of the two samples S1 and S2 are substantially coplanar. Two test samples A1 and B1 are resin molded into the sample S1, and two test samples A2 and B2 are resin molded into the sample S2. The XV stage 3 is driven by a drive mechanism (not shown in the drawings) driven in response to a control signal output by the controller 6. The XV stage 3 then displaces the sample stage 2 in a direction (X and Y directions) perpendicular to a displacement direction (Z direction) of the indenter 14a. The AF stage 4 is driven in response to the control signal output by the controller 6. The AF stage 4 then minutely raises and lowers the sample stage 2 based on the image data captured by the CCD camera 12 to focus on the surface of the sample S. The elevator mechanism 5 is driven in response to the control signal output by the controller 6. The elevator mechanism 5 then changes a relative distance between the sample stage 2 and the field lens 15 by displacing the sample stage 2 (the XV stage 3 and the AF stage 4) in the Z direction.

The console 7 is configured with a keyboard 71 and a mouse 72. The console 7 receives an operation input by an operator during a hardness test. In addition, when the console 7 receives a predetermined input operation performed by the operator, a predetermined operation signal corresponding to the input operation is generated and output to the controller 6. Specifically, the console 7 receives an operation in which the operator selects a condition determining a focus position of the indentation. The console 7 also receives an operation in which the operator designates a range of displacement (a range of relative distance between the sample stage 2 and the field lens 15) of the sample stage 2 (the elevator mechanism 5 and the AF stage 4). In addition, the console 7 receives an operation in which the operator inputs a test condition value to be used when carrying out the hardness test with the hardness tester 100. The input test condition value is transmitted to the controller 6. Herein, the test condition value is a value such as a material of the sample S, a test force (N) loaded on the sample S by the indenter 14a, or a magnification power of the field lens 15, for example. In addition, the console 7 receives an operation in which the operator selects one of a manual mode, in which the focus position of the indentation is manually determined, and an automatic mode, in which the determination is made automatically. The console 7 also receives an operation in which the operator programs a test position to be used when carrying out the hardness test.

The monitor 8 is configured by a display device such as an LCD, for example. The monitor 8 displays, for example, hardness test settings input on the console 7, results of the hardness test, and an image of the surface of the sample S and the indentation formed in the surface of the sample S captured by the CCD camera 12.

Figure 4:
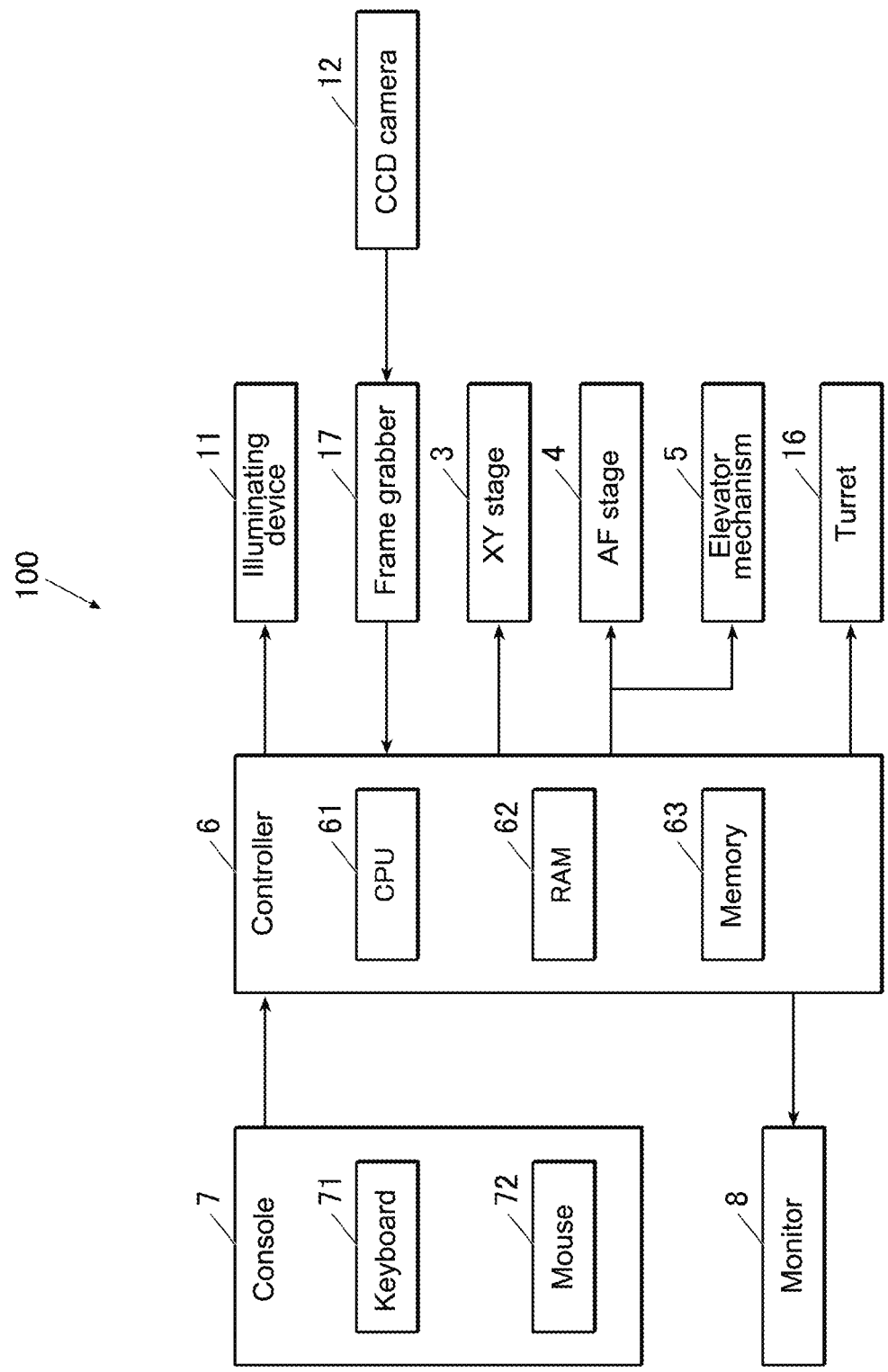
FIG. 4 is a block diagram illustrating a control structure of the hardness tester according to the present invention.

As shown in FIG. 4, the controller 6 is configured to include a CPU 61, a RAM 62, and a memory 63. The controller 6 performs operation control and the like of a predetermined hardness test by executing a predetermined program stored in the memory 63.

The CPU 61 retrieves a processing program and the like stored in the memory 63, then opens and executes the processing program in the RAM 62, thereby performing overall control of the hardness tester 100. The RAM 62 opens the processing program executed by the CPU 61 in a program storage region within the RAM 62 and stores in a data storage region input data, processing results generated during execution of the processing program, and the like. The memory 63 includes, for example, a recording medium (not shown in the drawings) storing a program, data, and the like. The recording medium is configured with a semiconductor memory, for example. In addition, the memory 63 stores various kinds of data, various kinds of processing programs, and data processed by running the programs that allow the CPU 61 to perform overall control of the hardness tester 100. In addition, the memory 63 stores test information defining a starting point and end point of profile detection of the sample S, as well as a hardness measurement position of the sample S, with reference to a pattern image selected based on the sample S (in the present embodiment, the various test samples A1, B1, A2, and B2).

Next, operations of the hardness tester 100 according to the present embodiment are described. First, the operator performs a process creating and registering the pattern image of the sample S as a preliminary stage of the hardness testing process shown in FIGS. 7 and 8. The registered pattern image is stored in the memory 63. This process may also be performed at the very beginning of the hardness testing process.

Next, a hardness testing process performed by the hardness tester 100 according to the present embodiment is described with reference to flow charts in FIGS. 7 and 8. First, as part of the hardness testing process, a process performed with the operator as agent is described with reference to the flow chart of FIG. 7.

First, the operator mounts two samples (S1 and S2) on the sample stage 2 and attaches the sample stage 2, with the mounted samples S1 and S2, at a predetermined position of the tester main body 10 (step S101).

Next, the operator launches software controlling the hardness tester 100 and activates the hardness tester 100, and defines various conditions of the hardness test (for example, material of the samples S1 and S2, test force, or magnification power of the field lens 15) (step S102).

Figure 9:
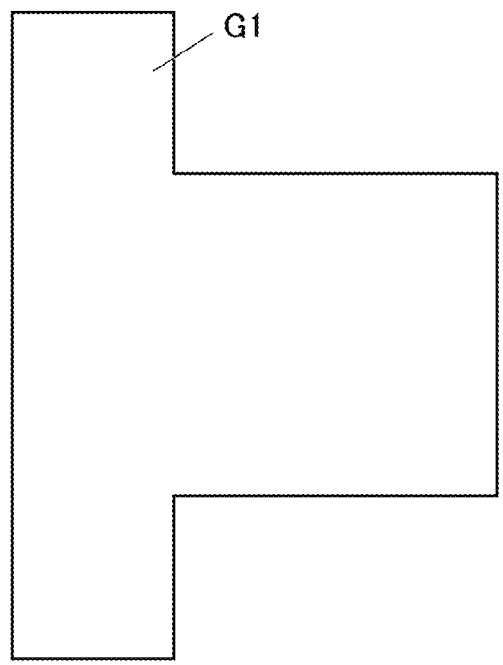
FIG. 9 illustrates an exemplary pattern image corresponding to a test sample.

Next, the operator selects the pattern image corresponding to each of the test samples A1 and B1, which are resin molded into the sample S1, and the test samples A2 and B2, which are resin molded into the sample S2 (step S103). FIG. 9 illustrates an exemplary pattern image G1 corresponding to the test sample A1.

Figure 10:
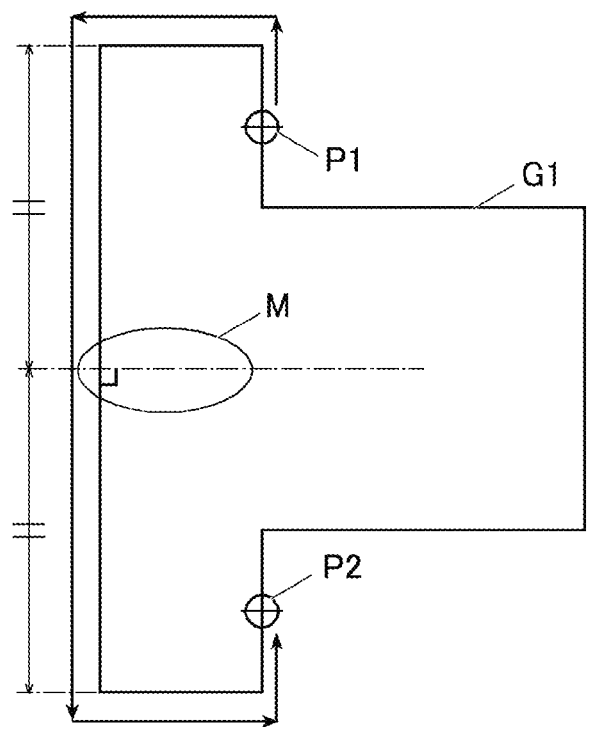
FIG. 10 illustrates an exemplary format indicating, on the pattern image corresponding to the test sample, a starting point and an end point of profile detection of the test sample.

Next, the operator designates, on each of the pattern images corresponding to the test samples and selected in step S103, the starting point and end point of profile detection of each test sample (step S104). For example, FIG. 10 illustrates an exemplary format where a starting point P1 and an end point P2 of the profile detection of the test sample A1 are designated on the pattern image G1 corresponding to the test sample A1.

Figure 11:
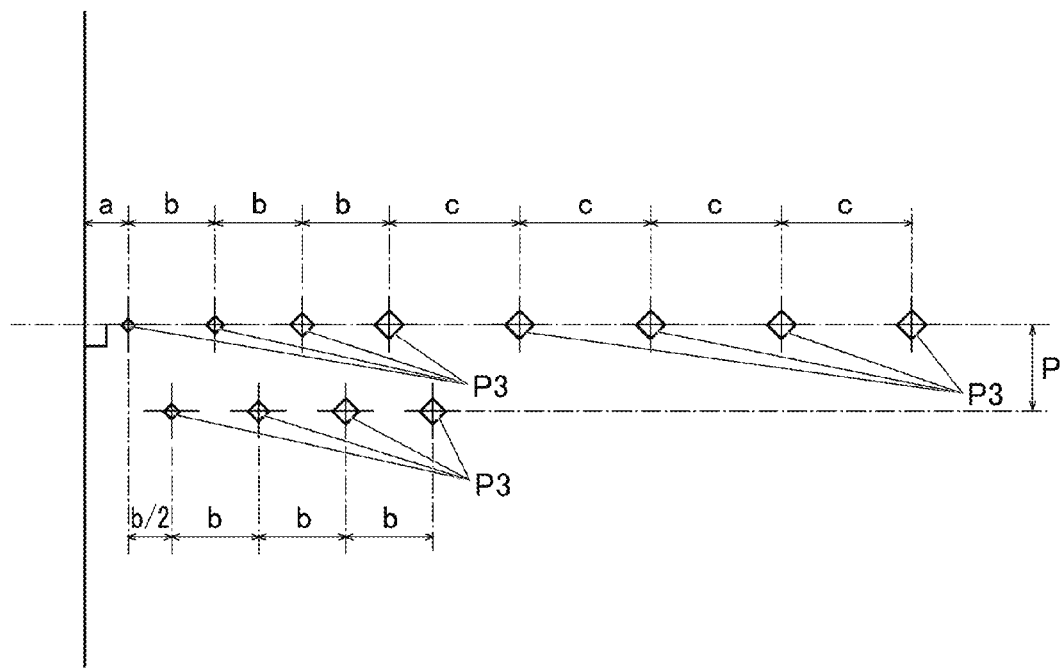
FIG. 11 is an enlarged view of a portion M in FIG. 10.

Next, the operator designates, on each of the pattern images corresponding to the test samples for which the starting point and the end point of profile detection are designated in step S104, both a coordinate system having the profile of the pattern image as a reference, and also the hardness measurement position (measurement pattern) of each of the test samples (step S105). For example, FIG. 11 illustrates an exemplary format where hardness measurement positions P3 of the test sample A1 are designated on the pattern image G1 corresponding to the test sample A1. The operator also inputs parameters such as a measurement interval. This information is stored in the memory 63 as test information defining the starting point and end point of profile detection of the sample S, as well as the hardness measurement position of the sample S, with reference to the pattern image selected based on the sample S (in the present embodiment, the various test samples A1, B1, A2, and B2). Moreover, the process from step S102 through step S105 may instead be configured as a process generating a settings file (test information) at a preliminary stage of the process shown in FIG. 7.

Next, as part of the hardness testing process, a process performed with the CPU 61 as agent is described with reference to the flow chart of FIG. 8. This process is initiated when an operation by the operator is detected giving an instruction to initiate automatic testing (for example, an operation where the operator uses the mouse 72 to click on an automatic testing initiation icon displayed on the monitor 8). In the present embodiment, the hardness test is conducted on, in order, the test sample A1 and the test sample B1 in the sample S1, and the test sample A2 and the test sample B2 in the sample S2.

First, the CPU 61 views the surface of the sample S1 (step S201). Specifically, the CPU 61 first rotates the turret 16 and switches to the field lens 15. Next, the CPU 61 operates the XY stage 3 such that the center of the sample S1 (see FIG. 5) is directly below the field lens 15. Next, the CPU 61 continuously acquires images with the CCD camera 12 while raising the AF stage 4, and calculates focus coordinates. Next, the CPU 61 operates the AF stage 4 and stops the AF stage 4 at the focus coordinates. Accordingly, the surface of the sample S can be viewed.

Next, the CPU 61 performs pattern searching of the test samples (step S202). Specifically, the CPU 61 first activates a pattern searching program which performs pattern searching on the test samples. The CPU 61 then acquires a focus image (searched object image) with the CCD camera 12 (image acquisition). Specifically, the CPU 61 is an image acquirer in the present invention. Next, the CPU 61 uses the pattern image corresponding to the test sample to be measured and performs pattern searching of the test sample with reference to the acquired searched object image (pattern searching). Specifically, the CPU 61 is a pattern searcher in the present invention. For example, in a case where the test sample A1 is to be measured, pattern searching of the test sample A1 is performed using the pattern image G1 (see FIG. 9) corresponding to the test sample A1.

Next, based on the starting point and end point of the profile detection of the test sample designated on the pattern image, the CPU 61 calculates the starting point and end point of the profile detection of the test sample on the searched object image (step S203). For example, in a case where the test sample A1 is to be measured, based on the starting point P1 and end point P2 of the profile detection of the test sample A1 designated on the pattern image G1, the CPU 61 calculates the starting point and end point of the profile detection of the test sample A1 on the searched object image. Next, the CPU 61 continuously executes profile detection from the starting point to the end point of the profile detection of the test sample calculated in step S203 and extracts the profile of the test sample (step S204: profile extraction). Specifically, the CPU 61 is a profile extractor in the present invention. For example, in a case where the test sample A1 is to be measured, the CPU 61 continuously executes profile detection from the starting point to the end point of the profile detection of the test sample A1 calculated in step S203 and extracts the profile of the test sample A1.

Next, the CPU 61 calculates the hardness measurement position of the test sample based on the profile extracted in step S204 and the hardness measurement position of the test sample designated on the pattern image (step S205: calculation). Specifically, the CPU 61 is a calculator in the present invention. For example, in a case where the test sample A1 is to be measured, the CPU 61 calculates the hardness measurement position of the test sample A1 based on the profile extracted in step S204 and the hardness measurement positions P3 of the test sample A1 designated on the pattern image G1.

Next, the CPU 61 operates the XY stage 3 such that, from among the hardness measurement positions calculated in step S205, the hardness measurement position to be measured next is directly below the field lens 15 (step S206). Next, the CPU 61 operates the AF stage 4 and performs a focusing operation. Accordingly, the sample to be measured (in a case where the test sample A1 is to be measured, the test sample A1) is positioned appropriately.

Next, the CPU 61 performs hardness testing and measures the hardness of the test sample to be measured (step S207: measurement). Specifically, the CPU 61 is a measurer in the present invention. Specifically, the CPU 61 first rotates the turret 16 and switches to the indenter 14*a*. Next, the CPU 61 performs indentation at the first hardness measurement position using the indenter 14*a*. Next, the CPU 61 rotates the turret 16 and switches to the field lens 15. Then, because there may be drift in the focus position clue to the indentation creation described above, the CPU 61 operates the AF stage 4 and performs another focusing operation. Next, the CPU 61 automatically reads the indentation formed by the indentation creation. Accordingly, hardness testing can be performed on the test sample to be measured (in a case where the test sample A1 is to be measured, the test sample A1) and the hardness of the test sample can be measured.

Next, the CPU 61 determines whether hardness testing has been performed at all of the hardness measurement positions (step S208). In a case where the CPU 61 determines that hardness testing has been performed at all of the hardness measurement positions (step S208: YES), the CPU 61 proceeds to the next step, S209. Meanwhile, in a case where the CPU 61 determines that hardness testing has not been performed at at least one of the hardness measurement positions (step S208: NO), the CPU 61 moves to step S206 and performs hardness testing at the unmeasured hardness measurement position.

Next, the CPU 61 determines whether hardness testing has been performed on all of the samples S (test samples) (step S209). In the present embodiment, the CPU 61 determines whether hardness testing has been performed on each of the test samples A1 and B1 of the sample S1 and test samples A2 and B2 of the sample S2, and when the CPU 61 determines that hardness testing has been performed for all of the samples S (step S209: YES), the process ends. Meanwhile, in a case where the CPU 61 determines that hardness testing has not been performed on at least one of the samples S (step S209: NO), the CPU 61 moves to step S201 and performs hardness testing on the unmeasured sample S.

As noted above, the hardness tester 100 according to the present embodiment includes: an image capturer/camera (CCD or other type of camera 12) capturing an image of the sample S to be measured; an image acquirer (CPU 61) acquiring image data of the sample S captured by the image capturer; a pattern searcher (CPU 61) performing, on the image data of the sample S acquired by the image acquirer, the pattern searching process using the pattern image selected based on the sample S (in the present embodiment, each of the test samples A1, B1, A2, and B2) and identifying a position in the image matching the pattern image; a profile extractor (CPU 61) extracting a profile of the sample S based on the position in the image identified by the pattern searcher; a calculator (CPU 61) calculating the hardness measurement position of the sample S based on the profile extracted by the profile extractor; and a measurer (CPU 61) executing hardness testing on the sample S based on the hardness measurement position calculated by the calculator and measuring the hardness of the sample S. Accordingly, a process of positioning the sample S so as to allow a hardness testing site to be displayed on the monitor 8 can be omitted with the hardness tester 100 of the present embodiment. Therefore, usability and work efficiency can be improved. In addition, when the process having the operator as agent ends, the process having the CPU as agent is automatically performed. Therefore, processes having the operator as agent are no longer interspersed with processes having the CPU as agent, and usability and work efficiency can be improved. Also, in a case where a plurality of samples S having an identical shape are tested, eliminating the intermingling of processes having the operator as agent and processes having the CPU as agent enables testing to be conducted simply by setting the sample S on the tester main body 100, beginning with the second sample S. This enables further improvement in work efficiency. Furthermore, eliminating the intermingling of processes having the operator as agent and processes having the CPU as agent allows the present invention to be readily introduced to an automated line, which enables a reduction in personnel costs associated with the work.

In addition, the hardness tester 100 according to the present embodiment includes a memory (the memory 63) storing test information defining the starting point and end point of the profile detection of the sample S, as well as the hardness measurement position of the sample S, with reference to the pattern image. Also, the profile extractor extracts the profile of the sample S based on the position in the image specified by the pattern searcher, and on the test information stored in the memory. The calculator calculates the hardness measurement position of the sample S based on the profile extracted by the profile extractor, and on the test information stored in the memory. Therefore, according to the hardness tester 100 of the present embodiment, so long as the test information is defined ahead of time, the profile of the sample S can be extracted and the hardness measurement position can be calculated automatically. This facilitates the operator's understanding of the task organization and enables the operator's time to be used effectively. Accordingly, work efficiency can be improved and personnel costs can be reduced.

In the above, a concrete description is given based on an embodiment according to the present invention. However, the present invention is not limited to the above-described embodiment and can be modified without deviating from the scope of the invention.

For example, in the above-described embodiment, the profile of the sample S is extracted and the hardness measurement position of the sample S is calculated based on the test information defining the starting point and end point of the profile detection of the sample S, as well as the hardness measurement position of the sample S, with reference to the pattern image. However, the present invention is not limited to this. For example, the hardness measurement position of the sample S may instead be calculated based on the extracted profile of the sample S and on a predetermined condition defined ahead of time. The predetermined condition may refer to, in the case of a round sample S, for example, a condition defining the hardness measurement position of the sample S, such as defining hardness measurement positions at a predetermined interval along an outer circumference (profile) of the sample S.

Figure 7:
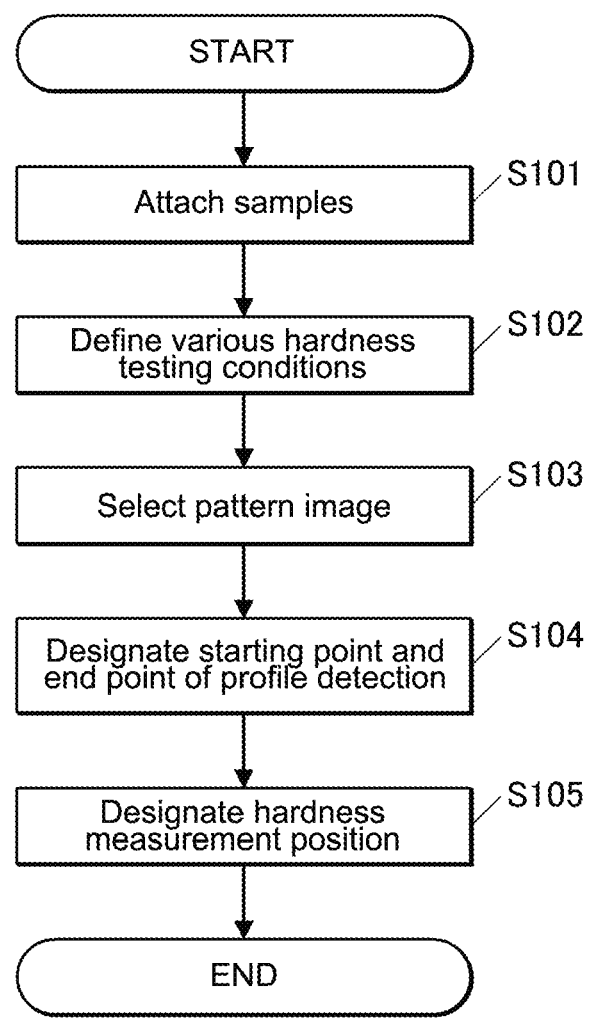
FIG. 7 is a flow chart illustrating a hardness testing process performed by the hardness tester according to an embodiment.
Figure 8:
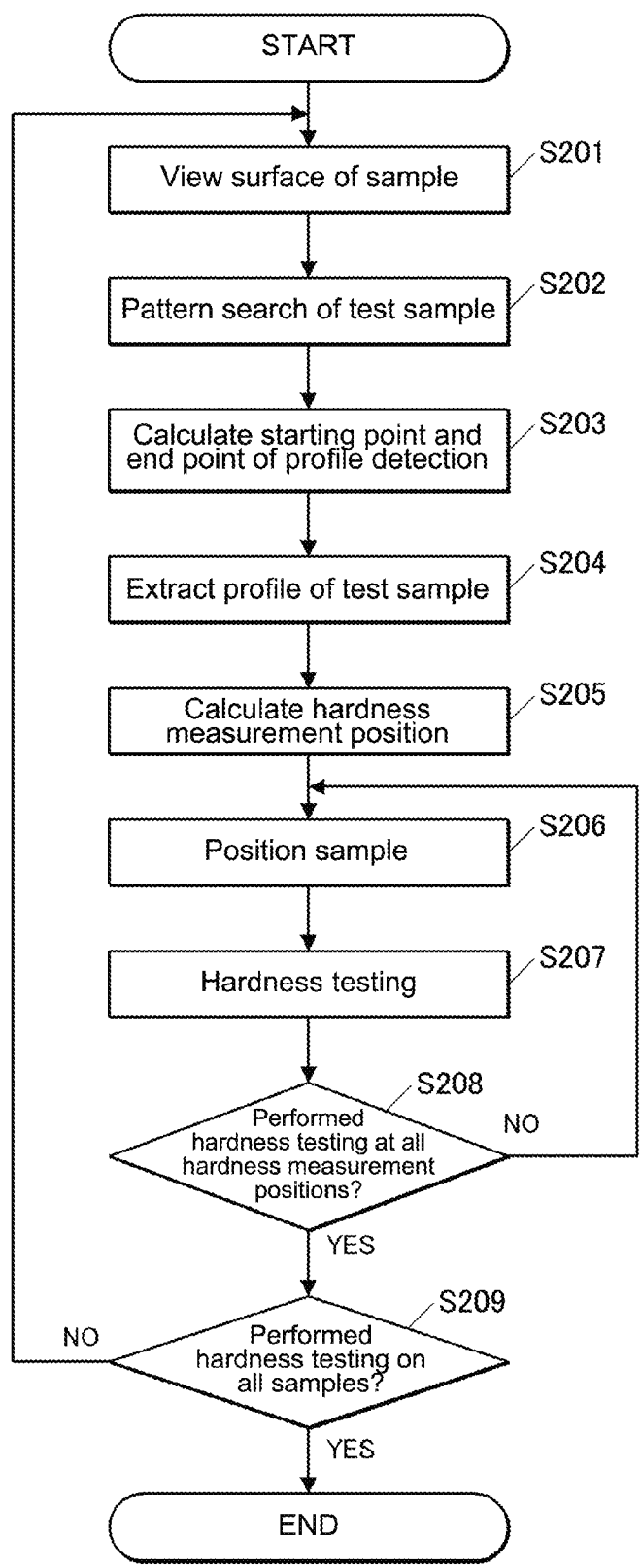
FIG. 8 is a flow chart illustrating the hardness testing process performed by the hardness tester according to the embodiment.

In addition, as shown in step S103 of FIG. 7, when the pattern image corresponding to the sample S (the various test samples A1, B1, A2, and B2) is selected, the above-described embodiment is configured such that the operator makes the selection. However, the present invention is not limited to this. For example, the present invention may instead be configured to acquire image data of the sample S and to automatically select a pattern image based on the acquired image data.

Also, when creating an indentation at the hardness measurement position in step S207 (shown in FIG. 8), the present invention may also be configured to determine whether there is any damage, dirt, or foreign body on the surface of the sample, for example. In a case where a foreign body or the like is present on the surface of the sample, the present invention may be configured to determine that the test area is not appropriate for hardness testing and to not perform indentation (hardness testing) in that area.

In addition, in the above-described embodiment, a Vickers hardness tester is described to exemplify the hardness tester 100. However, the present invention is not limited to this. The present invention may be applied to any hardness tester having an indenter with a known shape. For example, the present invention may also be applied to a Knoop hardness tester having a quadrangular pyramid diamond indenter.

In addition, within a scope not deviating from the substance of the present invention, appropriate modifications may also be made to detailed structures and operations of each component configuring the hardness tester 100.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester measuring hardness of a sample by loading a predetermined test force on the sample to form an indentation in a surface of the sample, then measuring dimensions of the indentation, the hardness tester comprising:
   a turret including an indenter which loads the predetermined test force on the sample to form the indentation in a surface of the sample,
   an image capturer capturing an image of the sample to be measured,
   an image acquirer acquiring image data of the sample captured by the image capturer;
   a pattern searcher performing, on the image data of the sample acquired by the image acquirer, a pattern searching process using a pattern selected based on the sample and identifying a position in the image matching the pattern, wherein the pattern is affixed to the sample;
   a profile extractor extracting a profile of the sample based on the position in the image identified by the pattern searcher;
   a calculator calculating a hardness measurement position of the sample based on the profile extracted by the profile extractor; and
   a measurer executing hardness testing by the indenter on the sample based on the hardness measurement position calculated by the calculator and measuring the hardness of the sample.

2. The hardness tester according to claim 1, further comprising:
a memory storing test information defining a starting point and end point of profile detection of the sample, as well as the hardness measurement position of the sample, with reference to the pattern image,
and wherein the profile extractor extracts the profile of the sample based on the position in the image specified by the pattern searcher, and on the test information stored in the memory, and
the calculator calculates the hardness measurement position of the sample based on the profile extracted by the profile extractor, and on the test information stored in the memory.

3. A hardness testing method of a hardness tester measuring hardness of a sample by loading a predetermined test force on the sample, then measuring dimensions of the indentation, the hardness testing method comprising:
loading the predetermined test force on the sample with an indenter to form an indentation on the surface of the sample;
acquiring image data of the sample;
performing, on the image data of the sample, a pattern searching process using a pattern selected based on the sample and identifying a position in the image matching the pattern, wherein the pattern is affixed to the sample;
extracting a profile of the sample based on the position in the image identified in the pattern searching process;
calculating a hardness measurement position of the sample based on the profile extracted in the extracting of the profile of the sample; and
executing hardness testing on the sample using the indenter based on the calculated hardness measurement position of the sample.

* * * * *